United States Patent [19]
Kaye et al.

[11] Patent Number: 5,217,015
[45] Date of Patent: Jun. 8, 1993

[54] PRESSURE SENSING DEVICE HAVING TRANSDUCER OVERLYING AND DEFORMING EYE

[76] Inventors: David B. Kaye, 2469 W. Roberts, Fresno, Calif. 93711; Charles D. Melville, 10559 N. Armstrong Ave., Fresno, Calif. 93612

[21] Appl. No.: 847,362

[22] Filed: Mar. 6, 1992

Related U.S. Application Data

[62] Division of Ser. No. 535,410, Jun. 8, 1990, Pat. No. 5,109,852.

[51] Int. Cl.$^5$ ................................................ A61B 3/16
[52] U.S. Cl. ..................... 128/645; 128/652; 73/754; 73/DIG. 4
[58] Field of Search .................. 128/645, 646, 652; 73/723, 727, 754, DIG. 4

[56] References Cited

U.S. PATENT DOCUMENTS 4,624,235 11/1986 Krabacher et al. ................ 128/652
4,628,938 12/1986 Lee ..................................... 128/652

Primary Examiner—Randy C. Shay
Attorney, Agent, or Firm—Worrel & Worrel

[57] ABSTRACT

A method for sensing pressure within a work object including placing an electrically deformable member on the work object so as to cover a portion of the surface area thereof; applying electrical energy to the member to cause the member to deform thereby applying pressure to the portion of the surface area of the work object; and sensing the tension in the member as a result of the amount of resistance to deformation imparted by the pressure within the work object.

An apparatus for sensing pressure within a work object including a member adapted to be disposed in overlaying relation to a portion of the surface area of the work object; an energizing system connected to the member for causing the member to deform so as to apply pressure to the surface area of the work object when disposed in overlaying relation to the work object to, in turn, cause the surface area of the work object to deform; and a detecting system operable to detect the magnitude of the deformation of the surface area of the work object as an indication of the pressure within the work object.

15 Claims, 3 Drawing Sheets

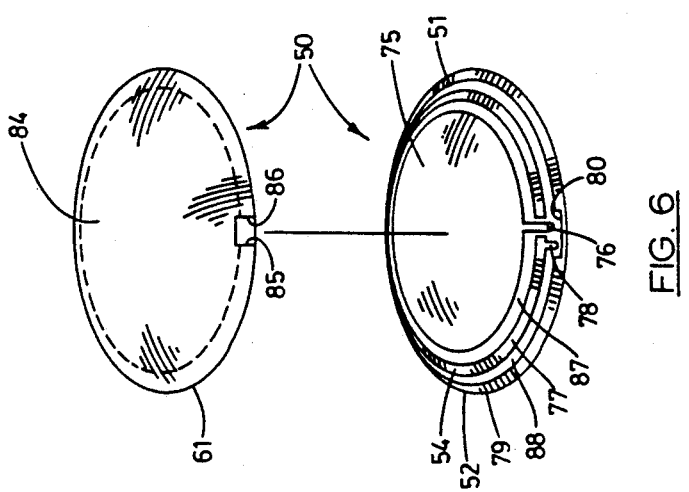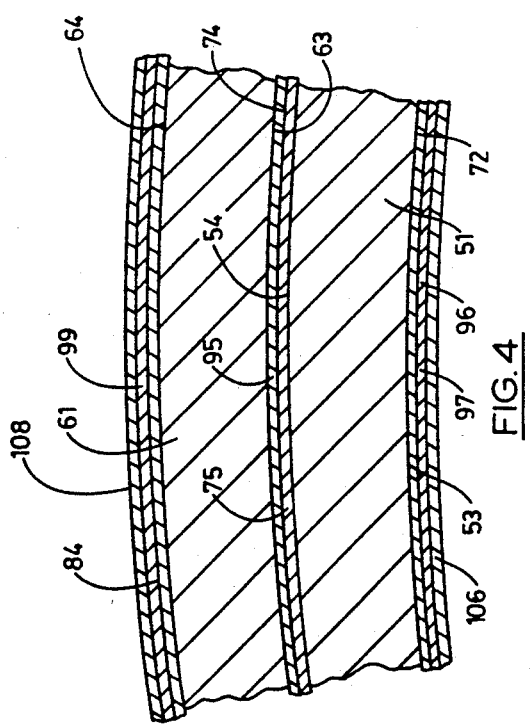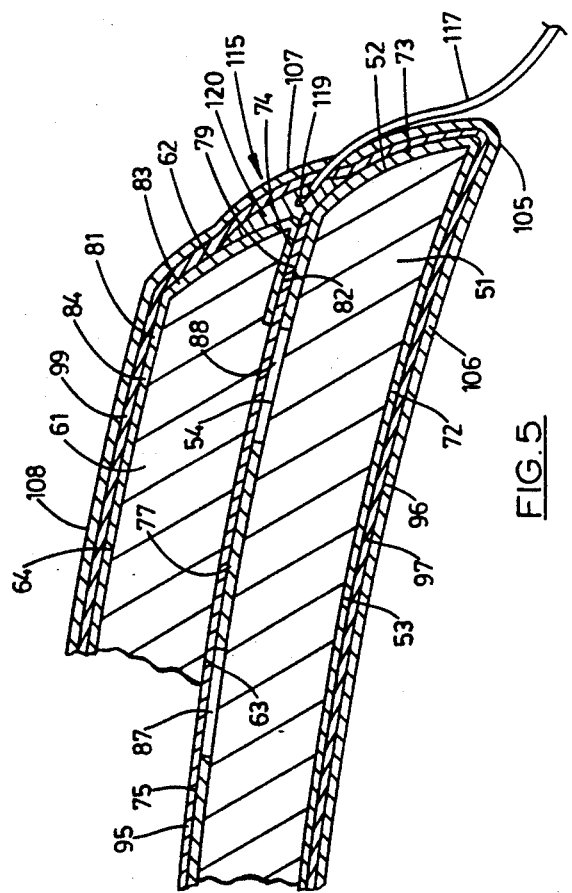

PRESSURE SENSING DEVICE HAVING TRANSDUCER OVERLYING AND DEFORMING EYE

This is a divisional of copending application(s) Ser. No. 07/535,410 filed on Jun. 8, 1990, now U.S. Pat. No. 5,109,852.

BACKGROUND OF THE INVENTION

1. Field of the Invention

The present invention relates to a method and apparatus for sensing pressure and, more particularly, to such a method and apparatus which are operable to permit the sensing of the internal pressure of pressurized work objects, such as the sensing of intraocular pressure, in a manner which is substantially more precise than has heretofore been possible.

2. Description of the Prior Art

The eye, or more precisely the eyeball, of humans and other living creatures, is a pressurized spherical vessel. The pressure, known as "intraocular pressure", serves to maintain the shape of the eyeball against collapse from ambient atmospheric pressure as well as acting in a variety of different ways to maintain the normal physiological functioning of the visual system. For example, intraocular pressure maintains the refracting capability of the cornea, supplies nourishment to the corneal layers, assists in retaining the stability of the retina, sclera and intraocular blood vessels, among its many functions. Thus, the maintenance of intraocular pressure within a normal range is of substantial importance for a number of significant reasons.

Abnormal variations in intraocular pressure are symptomatic of a host of diseases and abnormal physical conditions requiring treatment. Thus, the sensing of abnormal variations in intraocular pressure is critical to the diagnosis of such conditions. For example, glaucoma is a disease of the eye in which the aqueous humor of the eye does not drain normally resulting in an increase in intraocular pressure. If untreated, the condition ultimately destroys the optic nerve causing blindness.

The normal range of intraocular pressure is from about 10 to about 21 millimeters Hg. with the means being 16 millimeters Hg., plus or minus 2.5 millimeters Hg. However, intraocular pressure is subject to circadian rhythm such that, for example, the highest intraocular pressure for a given person is at about 6:00 a.m. In addition, the intraocular pressure is varied by blood pressure, heartbeat, respiration, season of the year, caffeine, other chemical substances, thyroid eye disease and a host of other factors. As a consequence, intraocular pressure is constantly fluctuating in reaction to all of these factors. When it is necessary or advisable to determine the intraocular pressure, it is impossible to predict when the most representative reading, for the particular purpose for which the intraocular pressure is to be checked, should be taken. Any single reading may thus be misleading and multiple readings taken at the same time every day, or on different equipment, or by different observers, or under different physiological or pathological conditions, may similarly be misleading. Thus, it has long been known that it would be highly advantageous to obtain both multiple and continuous readings over a lengthy period of time and extending over several days to as long as several weeks.

There are several conventional methods for measuring intraocular pressure. These can generally be categorized as direct and indirect methods. For example, in applanation tonometry, the force required to flatten 3.06 millimeters of the cornea is measured to provide the reading. Other electronic devices use smaller areas of contact. However, all such prior art methods are limited by their inability to provide a continuous reading over any substantial period of time; that is, they require the patient's presence at the test facility where the test equipment is located. Therefore, typically several individual measurements are taken over several days. This is both inconvenient to the patient and misleading for all of the reasons previously noted. There has not previously been a method by which, as a practical matter, the intraocular pressure could continuously be monitored over a length of time sufficient to provide reliable readings from which to diagnose disease or upon which medical decisions could be made. This absence of reliable data is particularly critical in the monitoring of low tension glaucoma and is even more acute where the patient is taking medication and where the other influencing conditions noted above prevail.

Therefore, it has long been known that it would be desirable to have a method and apparatus providing a means by which the internal pressure of work objects, such as the intraocular pressure of the human eye, could be determined over prolonged test periods to provide reliable data useful in detecting diseases such as glaucoma and abnormal physical conditions associated with the deviation from normal of intraocular pressure in a manner which is substantially more accurate and dependable than heretofore possible while being of little or no discomfort to the patient.

SUMMARY OF THE INVENTION

Therefore, it is an object of the present invention to provide an improved method and apparatus for sensing pressure.

Another object is to provide such a method and apparatus which are uniquely well suited to the sensing of intraocular pressure and providing the capability of taking substantially continuous readings over a prolonged period of several days to several weeks to show the entire range of fluctuation in intraocular pressure during that prolonged test period so as to take into account fluctuations resulting from normal factors, such as circadian fluctuation, blood pressure, heartbeat, respiration, seasonal variation, caffeine, and a multitude of other drug and systemic conditions, as well as abnormal conditions, such as glaucoma, thyroid eye disease and other diseases and abnormal physical conditions.

Another object is to provide such a method and apparatus which permit the physician to select the frequency with which such readings are taken during the test period as well as the length of the test period.

Another object is to provide such a method and apparatus which can be worn by the patient over a prolonged period of time substantially without care and with minimal discomfort while providing a substantial percentage of normal vision for the patient during the test period.

Another object is to provide such a method and apparatus which can be produced and used in a variety of different embodiments most suited to the particular data required and the conditions within which they will operate.

Another object is to provide such a method and apparatus which can be produced at relatively nominal costs.

Further objects and advantages are to provide improved elements and arrangements thereof in an apparatus for the purpose described which is dependable, economical, durable and fully effective in accomplishing its intended purpose.

These and other objects and advantages are achieved, in the preferred embodiment of the present invention, by placing an electrically deformable member on the work object so as to cover a portion of the surface area thereof; applying electrical energy to said member to cause the member to deform thereby applying pressure to said portion of the surface area of the work object; and sensing the tension in said member as a result of the amount of resistance to deformation imparted by the pressure within the work object.

BRIEF DESCRIPTION OF THE DRAWINGS

FIG. 4 is a substantially further enlarged, fragmentary cross section taken on line 4—4 in FIG. 1.

FIG. 5 is a substantially further enlarged, fragmentary cross section taken on line 5—5 in FIG. 1.

FIG. 6 is a somewhat reduced perspective exploded view of the sensing apparatus, but shown in a size enlarged beyond actual size.

DESCRIPTION OF THE PREFERRED EMBODIMENT

The sensing apparatus 10 has utility in a wide variety of operative environments and the specific environment herein discussed is not to be in any sense limiting. The method and apparatus hereof were particularly developed for and have unique operative advantages in connection with the sensing, in situ, of the intraocular pressure within the human eyeball throughout a long and substantially continuous test period covering several days or weeks. As previously noted, such continuous and reliable sensing has not heretofore been possible and has extraordinary benefits in the detection of glaucoma and other diseases and physical conditions. Accordingly, the method and apparatus are described herein in their application in this operative environment for illustrative convenience.

Figure 2:
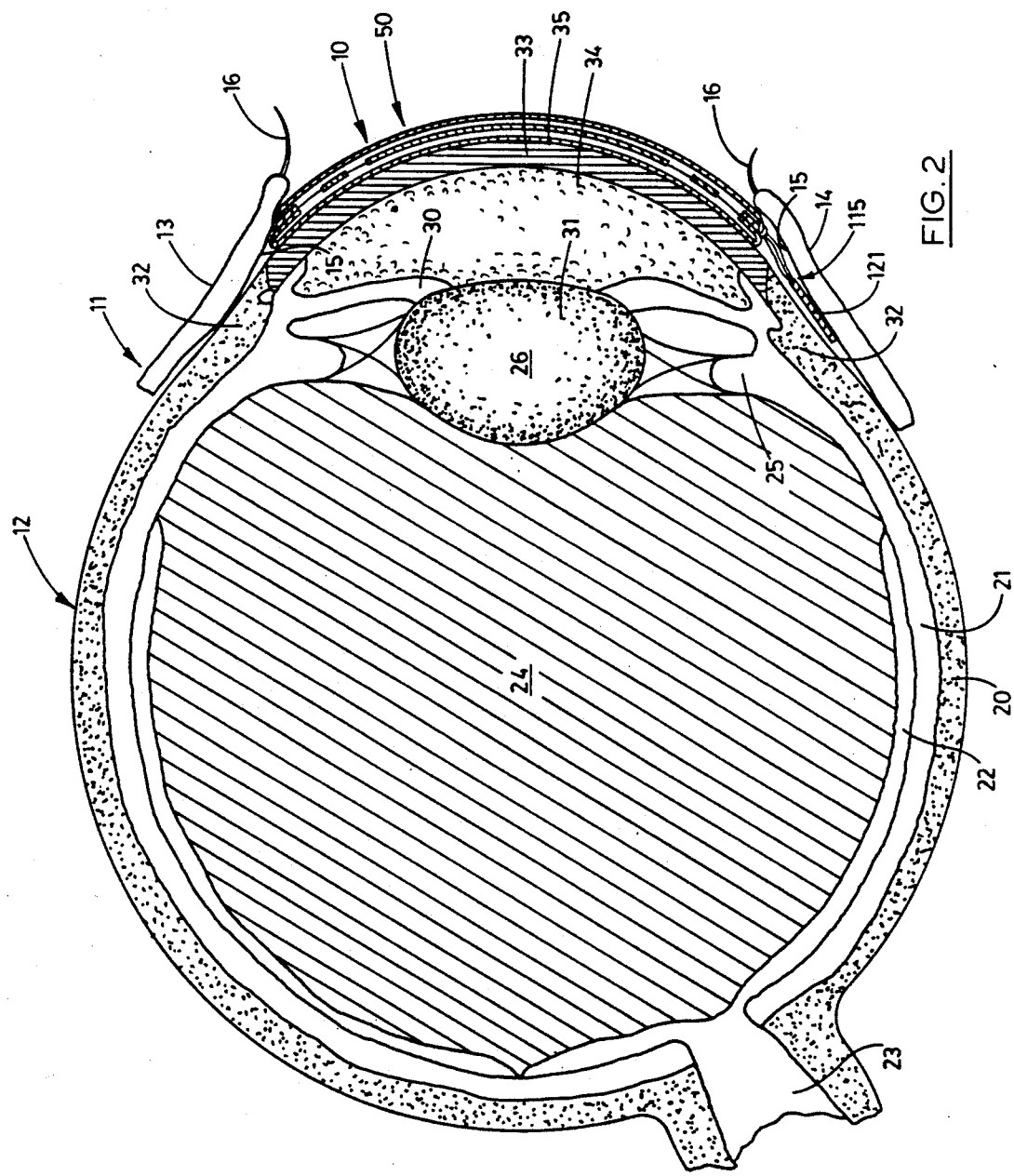
FIG. 2 is a cross section of the human eye enlarged substantially beyond actual size with the sensing apparatus shown in a typical operative position therein and with the sensing apparatus shown in cross section taken on line 2—2 in FIG. 1.

Referring more particularly to FIG. 2, the sensing apparatus 10 is adapted to be employed on and in connection with the human eye 11. As shown therein, the eye includes an eyeball 12, and upper eyelid 13 and a lower eyelid 14. The upper and lower eyelids have interior surfaces 15 and eyelashes 16.

The eyeball 12 is composed of a hemispherical sclera 20 which is lined with a choroid 21. A retina 22 is attached to the choroid on the left as viewed in FIG. 2. The optic nerve is indicated at 23. The sclera encloses the vitreous humor 24. The ciliary body 25 mounts the lens 26 of the eyeball 12 in spaced relation to the retina 22. An iris 30 overlays the lens 26 defining a pupil 31. The forward portion of the eyeball includes a conjunctiva 32 and a transparent cornea 33. The cornea encloses the aqueous humor 34. The cornea has an outer surface 35.

Figure 1:
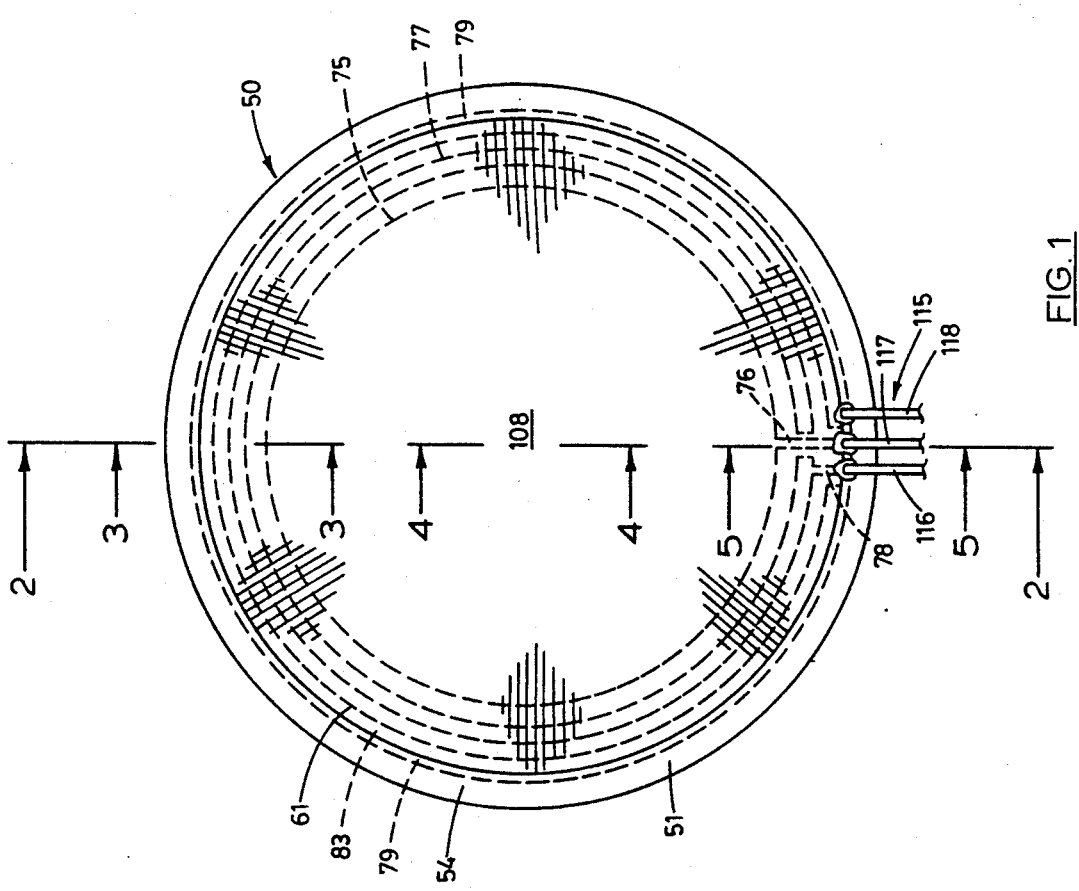
FIG. 1 is a top plan view of the sensing apparatus of the present invention adapted to practice the method hereof and shown substantially enlarged from actual size.

The sensing apparatus 10 of the present invention includes a transducer, contact lens or sensing member 50 which is shown intact in FIG. 1, but which can perhaps best be understood upon reference to the other views of the drawings. The sensing member has a transparent inner film layer 51 which is a hemisphere bounded by a substantially circular peripheral edge 52 and having a concave lower surface 53 and an opposite convex upper surface 54. The sensing member has a transparent outer film layer 61 which forms a hemisphere and which has a circular peripheral edge 62. The outer film layer has a concave lower surface 63 and an opposite convex upper surface 64. While the sensing member can be constructed of a variety of different materials, it has been found that piezoelectric film, such as that manufactured under the trademark "KYNAR" by Pennwalt Corporation of Valley Forge, Pa., is excellently suited to the purpose.

Inner and outer film layers 51 and 61, respectively, are constructed of piezoelectric film with the piezo strain constants in the $d_{31}$ and $d_{32}$ directions being equal in value. The piezoelectric film polling of film layers 51 and 61, respectively, is in the $d_{33}$ direction and the polling of film layer 51 is opposite the polling of film layer 61.

The inner film layer 51 has metallization 71 thereon in areas hereinafter to be described. A metallization hereinafter described on the inner and outer film layers 51 and 61, respectively, is extremely thin being only a few atoms thick. The sensing member, though having surfaces of metallization, is substantially transparent such as to permit light transmission therethrough having a value of approximately seventy-five percent (75%) of full transparency.

The metallization 71 of the inner film layer 51 includes a metallization surface 72 covering the entire concave lower surface 53 of the inner film layer. The metallization 71 further includes a metallization surface 73 extending about the peripheral edge 52 of the inner film layer. A metallization surface 74 extends over the convex upper surface 54 of the inner film layer, as can perhaps best be seen in FIGS. 3 and 5, in patterns hereinafter to be described. The metallization surface 74 has a central pattern of metallization 75 forming a substantially circular hemisphere on the convex upper surface 54 substantially concentric to the peripheral edge 52 of the inner film layer 51. The central pattern has an electrode portion 76 extending toward the peripheral edge 52. The metallization surface 74 further has an annular pattern of metallization 77 formed on the convex upper surface 54 spaced from and concentric to the central pattern of metallization. The annular pattern of metallization has an electrode portion 78. The metallization surface 74 still further includes a peripheral pattern 79 spaced outwardly from and concentric to the annular pattern of metallization. A notch 80 is formed in the peripheral pattern of metallization 79 spaced from the electrode portions 76 and 78.

The outer film layer 61 has metallization 81 formed thereon. The metallization includes a metallization surface 82 formed on the concave lower surface 63 just over lapping the peripheral edge thereof and leaving the substantial portion of the concave lower surface 63 free of such metallization. The metallization 81 further includes a metallization surface 83 extending about the peripheral edge 62 of the outer film layer 61. Metallization surface 84 extends substantially over the entire convex upper surface 64 of the outer film layer, the exception being a notch 85 formed in the metallization surface 82 and the notch 86 formed in metallization surface 84.

As best shown in FIG. 6, the central pattern of metallization 75 of the inner film layer 51 and the annular pattern 77 thereof are spaced from each other by a fully transparent annulus 87. Similarly, the annular pattern 77 is spaced from the peripheral pattern 79 by a fully transparent annulus 88.

The inner film layer 51 and the outer film layer 61, and the metallization 71 and 81 respectively thereof, are bonded together by a suitable adhesive layer 95 extending therebetween so that the outer film layer 61 overlays the inner film layer 51 in substantially concentric relation as can perhaps best be seen in FIG. 1. A variety of suitable adhesives can be employed, but it is preferred that the adhesive, when dried, be transparent for purposes subsequently to be described. Some suitable adhesives where "KYNAR" piezoelectric film is employed for layers 51 and 61 are Tycel 7000/7200, Bostic 7132, RBC3215, Devcon 5 min., PM 204, Conastic AD20. When so bonded together, the outer and inner film layers, and the areas of metallization thereof are disposed in relation thereto as best shown in FIGS. 3, 4 and 5.

Figure 3:
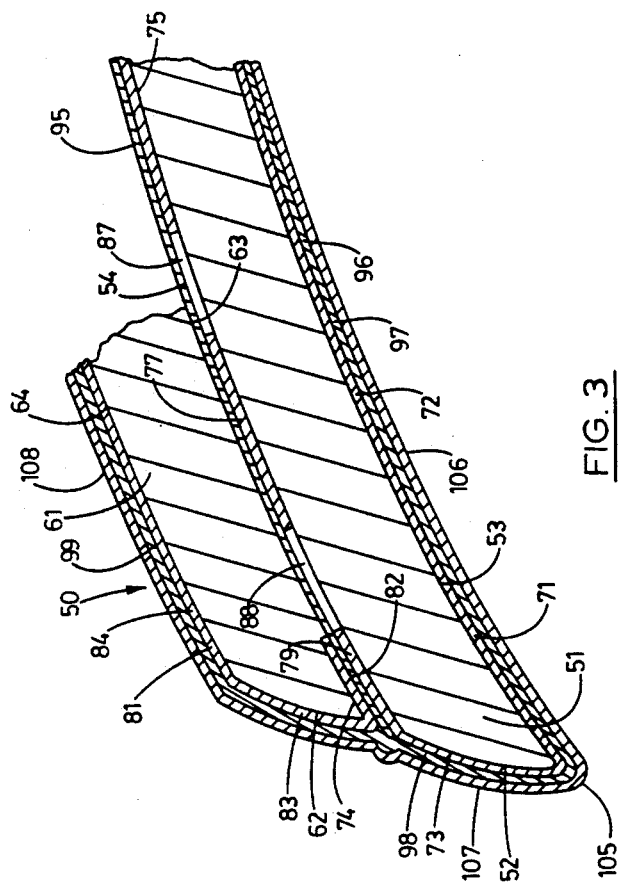
FIG. 3 is a substantially further enlarged, fragmentary cross section taken on line 3—3 in FIG. 1.

As can perhaps best be visualized in FIGS. 3 and 5, the metallization surface 82 of outer film layer 61 engages the peripheral pattern 79 of the inner film layer 51 in electrically conductive relation through the adhesive layer 95 and receives electrical energy from the third wire 118 through the electrically conductive adhesive 120. As previously noted, the central pattern of metallization 75 receives electrical energy from the second wire 117 through electrode portion 76. The annular pattern of metallization 77 transmits electrical energy to the first wire 116 through electrode portion 78. Thus, the areas of metallization of the sensing member can be viewed as defining a first electrically conductive zone composed of the central pattern of metallization 75, a second electrically conductive zone composed of the annular pattern of metallization 77, and a third electrically conductive zone composed of metallization surfaces 72, 73 and the peripheral pattern 79 of metallization surface 74 and all of metallization 81, that is metallization surface 82, 83 and 84.

The sensing member 50 is covered with a layer of electrically insulating film 96 of a transparent type to preclude electrical shock to the patient. The insulation film includes a lower portion 97 covering the entire metallization surface 72 of the inner film layer 51, a peripheral portion 98 covering the metallization surfaces 73 and 83 of the inner and outer film layers and an upper portion 99 covering the entire metallization surface 84 of the convex upper surface 64 of outer film layer 61.

The entire sensing member 50 is encapsulated in a transparent hydrophilic layer 105 operable to insure sufficient wetting or lubrication of the sensing member for the use subsequently to be described. The hydrophilic layer includes a lower portion 106 extending entirely across the lower portion 97 of the insulation film 96, a peripheral portion 107 extending entirely across and about the peripheral portion 98 of the insulation film and an upper portion 109 extending entirely across the upper portion 99 of the insulation film. Thus, the entire sensing member is encapsulated in a hydrophilic layer so as to constitute a unitary body.

The sensing apparatus 10 includes an electrical assembly generally indicated by the numeral 115. The electrical assembly includes a first wire 116 which is electrically connected to the electrode portion 78 of the annulus pattern 77, as can best be seen in FIG. 1. A second wire 117 is electrically connected to the electrode portion 76 of the central pattern of metallization 75. a third wire 118 is electrically connected to the metallization surfaces 73 of the inner film layer 51 and 83 of the outer film layer 61. The wires are all of very fine gauge. Each of the wires 16, 17 and 18 includes a looped exposed end 119 which is attached to the portions heretofore described by electrically conductive adhesive 120, as best shown in FIGS. 1 and 5.

The electrical assembly 115 includes a wafer or wafer-like transmitter/receiver 121 shown in FIG. 2. The transmitter/receiver is electrically connected to the first wire 116, the second wire 117, and the third wire 118. The transmitter/receiver is a very small, flat and thin device which, through microtechnology, houses a battery, not shown, a transmitter, not shown and a receiver, not shown. Any suitable wafer-like transmitter/receiver will serve the purpose. It will be understood, however, that the sensing member can be directly connected to any suitable detecting and recording system either carried on the body of the patient or connected to a larger and more elaborate transmitter/receiver as best suited to the particular demands of the operation to be performed as determined by the physician.

OPERATION

The operation of the described embodiment of the subject invention is believed to be clearly apparent and is briefly summarized at this point.

The sensing member 50, when constructed as heretofore described, is substantially transparent permitting approximately seventy-five percent (75%) light transfer therethrough principally because of the thinness of the various layers composing the sensing member. Similarly, the sensing member as a whole is very thin proximating the thickness and diameter of a soft contact lens and dimensioned to overlay the cornea 33 of the eyeball 12 and, in some instances a small portion of the conjunctive 32 of the eyeball.

In any case, the sensing member 50 is placed in overlaying relation to the outer surface 35 of the cornea 33 with the lower portion 106 of the hydrophilic layer 105 of the sensing member in direct contact with the outer surface 35, as can best be seen in FIG. 2. The peripheral edges of the sensing member normally fit just beneath the upper and lower eyelids 13 and 14, respectively. The wafer-like transmitter/receiver 121 is positioned preferably between the interior surface 15 of the lower eyelid 14 and the conjunctiva 32 of the eyeball 12 also as shown in FIG. 2.

Once installed as described, the sensing apparatus 10 is ready for operation. It is intended that the patient wearing the sensing apparatus 10 on one or both eyes continue to wear the sensing apparatus through the daylight hours and, if prescribed by the physician, during the nighttime hours as well. A microcontroller, not shown, worn by the patient or in close proximity to the patient is employed automatically to send and receive signals to and from the transmitter/receiver 121. Thus, the patient has vision through the sensing member to approximately seventy-five percent (75%) of normal light transmission while the sensing operation is taking place. As previously noted, this test period may be one day, several days, or a week or more as the physician may prescribe.

During wearing of the sensing apparatus 10, the microcontroller operates to send periodic signals to the transmitter/receiver 121. When this takes place, the transmitter/receiver closes an electrical circuit, not shown, to supply electrical energy through the second and third electrical wires 117 and 118 to the first and third electrically conductive zones of the sensing member. The energizing of the central pattern of metallization 75 causes the central portions of the inner and outer film layers 51 and 61, respectively, to contract thus moving the central portion of the sensing member toward a less curved condition. This applies pressure to the cornea 33 in the direction of the lens 26 of the eyeball 12. The intraocular pressure within the eyeball resist such deformation of the cornea so that the deformation of the central portion of the sensing member cannot fully take place as would otherwise be the case.

In any case, deformation of the central portion of the sensing member 50 causes tension in the film layers 51 and 61 between the second and third electrically conductive zones dependent upon the resistance provided by intraocular pressure within the eyeball. The amount of tension created is directly proportional to the intraocular pressure within the eyeball. This tension creates a corresponding electrical potential between the second and third electrically conductive zones which is directly proportional as well to the intraocular pressure within the eyeball. This electrical potential is sensed by the transmitter/receiver and is transmitted by an electrical signal, radio wave, light plus or by any other suitable means to the microcontroller in the vicinity which records the reading.

The cycle of operation is repeated, at the selection of the physician, as controlled by the microcontroller so that repeated readings are taken over the test period, which, as noted, may be several days, a week or more. As a consequence, the readings so produced are employable to calculate the intraocular pressure of the eyeball under virtually all conditions and throughout a prolonged test period. This has never before been possible and permits the tabulation of data which is highly beneficial in detecting the onset of glaucoma, other diseases or physical conditions. The patient, during such usage, is subjected to little or no discomfort over the period of usage and retains vision approaching the patient's normal vision during the test period.

Therefore, the method and apparatus of the present invention provide a means by which the internal pressure of work objects, such as the intraocular pressure of the human eye, can be determined over a prolonged test period to provide data useful in detecting diseases such as glaucoma and abnormal physical conditions associated with the deviation from normal of intraocular pressure in a manner which is both substantially more accurate and dependable while being of little or no discomfort to the patient and being of minimal cost and substantial convenience.

Although the invention has been herein shown and described in what is conceived to be the most practical and preferred embodiment, it is recognized that departures may be made therefrom within the scope of the invention which is not to be limited to the illustrative details disclosed.

Having described our invention, what we claim as new and desire to secure by Letters Patent is:

1. An apparatus for sensing pressure within a work object having a surface area, the apparatus comprising a transducer adapted to be disposed in overlaying relation to a portion of the surface area of said work object; means connected to said transducer for causing the transducer to deform so as to apply pressure to the surface area of said work object when disposed in said overlaying relation thereto, in turn, to cause said surface area of the work object to deform; and means for detecting the magnitude of the deformation of the surface area of the work object as an indication of the pressure within said work object.

2. An apparatus for sensing pressure within a work object having a surface area, the apparatus comprising a transducer, operable to deform upon the application of electrical energy thereto, adapted to be disposed in overlaying relation to a portion of the surface area of said work object; a source of electrical energy connected in electrical energy supplying relation to said transducer and operable selectively to apply electrical energy to said transducer to cause the transducer to deform so as to apply pressure to the surface area of said work object when disposed in said overlaying relation thereto, in turn, to cause said surface area of the work object to deform; and means for detecting the magnitude of the deformation of the surface area of the work object as an indication of the pressure within said work object.

3. The apparatus of claim 2 wherein said transducer has an electrically conductive area connected in electrical energy receiving relation to said source of electrical energy operable, upon the application of electrical energy thereto, to contract the transducer causing said deformation thereof.

4. The apparatus of claim 3 wherein said transducer has second and third electrically conductive areas electrically isolated from each other and from said first electrically conductive area and operable, upon said application of electrical energy to the first electrically conductive area, to create an electrical potential proportional to said deformation of the transducer as permitted by the deformation of said surface area of said work object.

5. The apparatus of claim 4 wherein said transducer is constructed of at least two layers of piezoelectric film containing said first, second and third electrically conductive areas.

6. The apparatus of claim 4 wherein the first electrically conductive area is bounded by said second and third electrically conductive areas whereby said contraction of the transducer is substantially coincident with the first electrically conductive area causing tension in the transducer between the second and third electrically conductive areas to create said electrical potential.

7. The apparatus of claim 6 in which said work object is an eyeball having an intraocular pressure and a cornea and wherein the transducer is constructed of at least two layers of piezoelectric film containing said first, second and third electrically conductive areas as discrete, substantially transparent layers of metallization forming a contact lens adapted to be placed in overlaying relation on said cornea of the eyeball for measuring the intraocular pressure of the eyeball.

8. The apparatus of claim 7 in which the eyeball is bounded by eyelids and wherein said source of electrical energy is embodied in a wafer adapted to be disposed between the eyelid and eyeball.

9. The apparatus of claim 8 wherein said wafer houses, in addition to said source of electrical energy, a transmitter/receiver operable upon receiving a signal from a remote location to apply said electrical energy from the source of electrical energy to the first, second and third electrically conductive areas and upon the detecting of said electrical potential to transmit a signal representative of said electrical potential to a remote location.

10. An apparatus for sensing the intraocular pressure within the human eyeball having a cornea, the apparatus comprising:

A. a first transparent film having opposite inner and outer surfaces, a periphery and an outer substantially transparent layer of electrically conductive metallization extending over substantially the entire outer surface, the periphery and a portion of the inner surface;

B. a second transparent film having opposite inner and outer surfaces, a periphery and a central substantially transparent layer of electrically conductive metallization extending over a substantial portion of the inner surface in spaced relation to said periphery of the second film, an annular substantially transparent layer of electrically conductive metallization extending over the inner surface about said central layer in spaced relation to the periphery thereof and in spaced relation to the periphery of the second film and an outer substantially transparent layer of electrically conductive metallization extending over substantially the entire outer surface of the second film, the periphery and a portion of the inner surface about said annular layer and in spaced relation thereto;

C. a substantially transparent adhesive bonding said inner surface of the first film in overlaying relation on said inner surface of the second film with said outer layer of metallization of the first film in electrically conductive relation to said outer layer of metallization of the second film and electrically isolated from said central and annular layers of metallization of the second film whereby the central layer of metallization is a first electrically conductive zone, the annular layer is a second electrically conductive zone and the outer layers of metallization of the first and second films compose a third electrically conductive zone;

D. a source of electrical energy individually connected to said first and third electrically conductive zones;

E. means for selectively applying electrical energy from said source of electrical energy to the first and third electrically conductive zones so that said first electrically conductive zone causes the first and second films to contract whereby when said apparatus is disposed in overlaying relation on the cornea of the eyeball pressure is applied to the cornea against said intraocular pressure within said eyeball and creating tension in the first and second films about the first electrically conductive zone and between said second and third electrically conductive zones to create an electrical potential therebetween proportional to the intraocular pressure within said eyeball; and F. means for detecting said electrical potential between the second and third electrically conductive zones as in index of the intraocular pressure within the eyeball.

11. The apparatus of claim 10 in which the eyeball is bounded by an eyelid and wherein said source of electrical energy is a battery housed in a wafer and individually connected to the first and third electrically conductive zones by fine electrical conductors and said wafer is adapted to be disposed between said eyelid and the eyeball when said apparatus is disposed in overlaying relation on the cornea of the eyeball.

12. The apparatus of claim 11 wherein said applying means includes a receiver mounted in said wafer and operable, upon receipt of a signal from a remote location, to cause electrical energy to pass from the battery along said electrical conductors to the first and third electrically conductive zones.

13. The apparatus of claim 12 wherein said detecting means includes a transmitter mounted in said wafer and operable to detect said electrical potential between the second and third electrically conductive zones and to transmit a signal to a remote location representative of said electrical potential.

14. The apparatus of claim 10 wherein the first and second films and the first, second and third electrically conductive zones are sealed in a substantially transparent electrically insulating layer to preclude electrical shock.

15. The apparatus of claim 14 wherein the electrically insulating layer, the first and second films and the first, second and third electrically conductive zones are sealed in a substantially transparent hydrophilic layer for lubrication to insure releasable adhesion to the cornea.

* * * * *

UNITED STATES PATENT AND TRADEMARK OFFICE
CERTIFICATE OF CORRECTION

PATENT NO. : 5,217,015
DATED : June 8, 1993
INVENTOR(S) : DAVID B. KAYE and CHARLES D. MELVILLE It is certified that error appears in the above-identified patent and that said Letters Patent is hereby corrected as shown below:

Column 6, line 48, delete "conjunctive" and substitute ---conjunctiva---.

Signed and Sealed this

First Day of February, 1994

Attest:

BRUCE LEHMAN

Attesting Officer     Commissioner of Patents and Trademarks